US008652808B2

(12) United States Patent
Jennewein et al.

(10) Patent No.: US 8,652,808 B2
(45) Date of Patent: Feb. 18, 2014

(54) METHOD FOR THE PRODUCTION OF FUCOSYLLACTOSE IN BACTERIAL CELLS

(75) Inventors: Stefan Jennewein, Aachen (DE); Eric Huefner, Hennef (DE); Julia Parkot, Cologne (DE)

(73) Assignee: Jennewein Biotechnologie GmbH, Rheinbreitbach (DE)

( * ) Notice: Subject to any disclaimer, the term of this patent is extended or adjusted under 35 U.S.C. 154(b) by 0 days.

(21) Appl. No.: 13/308,082

(22) Filed: Nov. 30, 2011

(65) Prior Publication Data
US 2012/0135467 A1 May 31, 2012

Related U.S. Application Data

(63) Continuation of application No. PCT/EP2009/004112, filed on Jun. 8, 2009.

(51) Int. Cl.
*C12N 1/15* (2006.01)

(52) U.S. Cl.
USPC ......................................... 435/72; 435/252.3

(58) Field of Classification Search
None
See application file for complete search history.

(56) References Cited

FOREIGN PATENT DOCUMENTS

| EP | 08172267 | 12/2008 |
|---|---|---|
| WO | 99/11773 | 3/1999 |

OTHER PUBLICATIONS

Chica et al., Semi-rational approaches to engineering enzyme activity: combining the benefits of directed evolution and rational design. Current Opinion Biotechnol. 2005, 16(4): 378-84.*
Sen et al. Developments in Directed Evolution for Improving Enzyme Functions. Appl. Biochem. Biotechnol. 2007, 143(3): 212-23.*
Alaimo, C., et al., (2006) Two distinct but interchangeable mechanisms for flipping of lipid-linked oligosaccharides. EMBO J 25 (5): 967-976.
Albermann, C., et al., (2001) Synthesis of the milk oligosaccharide 2'-fucosyllactose using recombinant bacterial enzymes. Carbohydr Res 334: 97-103.
Andersson, B., et al, (1986) Inhibition of attachment of *Streptococcus pneumonia* and *Haemophilus influenzae* by human milk and receptor oligosaccharides. J Infect Dis 153: 232-237.
Bode, L., (2006) Recent advances on structure, metabolism, and function of human milk oligosaccharides. J Nutr 136:2127-2130.
Boehm, G & B Stahl, (2007) Olgosaccharides from milk. J Nutr 137: 847S-849S.
Condemine, Guy, "Characterization of SotA and SotB, Two *Erwinia chrysanthemi* Proteins Which Modify Isopropyl- β-D-Thiogalactopyranoside and Lactose Induction of the *Escherichia coli* lac Promoter," Journal of Bacteriology, Mar. 2000, pp. 1340-1345.

Coppa, G. V., et al., (2006) Human milk oligosaccharides inhibit the adhesion to Caco-2 cells of diarea pathogens: *Escherichia coli*, *Vibrio cholerae*, and *Salmonella fyris*. Pediatr Res 59: 377-382.
Coyne, M. J., et al., (2005) Human symbionts use a host-like pathway for surface fucosylation. Science 307: 1778-1781.
Crane, J. K., et al., (1994) Olgosaccharides from human milk block binding and activitiy of the *Escherichia coli* heatstable enterotoxin (STa) in T84 intestinal cells. J Nutr 124: 2358-2364.
Cravioto, A., et al., (1991) Inhibition of localized adhesion of enteropathogenic *Escherichia coli* to HEp-2 cells by immunoglobulin and oligosaccharide fractions of human colostrums and breast milk. J Infect Dis 163: 1247-1255.
Datsenko, K. A., et al., (2000) One-Step inactivation of chromosomal genes in *Escherichia coli* K-12 using PCR products. Proc Natl Aced Sci U S A 97: 6640-5.
Dower, W. J., et al., (1988) High efficiency transformation of *E. coli* by high voltage electroporation. Nucleic Acids Res 16: 6127-45.
Dumon, C, et al., (2001) In vivo fucosylation of lacto-N-neotetraose and lacto-N-neohexaose by heterologous expression of *Helicobacter pylori* alpha-1, 3 fucosyltransferase in engineered *Escherichia coli*. Glycoconj J 18: 465-474.
Dumon, C, et al., (2004) Assessment of the two *Helicobacter pylori* alpha-1, 3-fucosyltransferase ortholog genes for the large-scale synthesis of LewisX human milk oligosaccharides by metabolically engineered *Escherichia coli*. Biotechnol Prog 20: 412-419.
Dumon, C, et al., (2006) Production of Lewis x tetrasaccharides by metabolically engineered *Escherichia coli*. Chembiochem 7: 359-365.
Gnoth, M. J., et al., (2001) Investigation of the in vitro transport of human milk oligosaccharides by a Caco-2 monolayer using a novel high performance liquid chromatography-mass spectrometry technique. J Biol Chem 276: 33463-34370.
Grant, W. D., et al. (1970) Control of colonic acid synthesis. J Bacteriol 103: 89-96.
International Preliminary Report on Patentability mailed Dec. 12, 2011, International Patent Application No. PCT/EP2009/004112.
Ishihara, Hisamitsu, et al., "Overexpression of monocarboxylate transporter and lactate dehydrogenase alters insulin secretory responses to pyruvate and lactate in β cells", The Journal of Clinical Investigation, Dec. 1999, vol. 104, No. 11, pp. 1621-1629.
Koizumi, S., et al., (2000) Large-scale production of GDP-fucose and Lewis X by bacterial coupling. J Ind Microbiol Biotechnol 25: 213-217.

(Continued)

*Primary Examiner* — Tekchand Saidha
*Assistant Examiner* — Rama P Ramanujam
(74) *Attorney, Agent, or Firm* — Casimir Jones SC (57) ABSTRACT

The present invention relates to a cell to be stably cultured in a medium, which cell is adjusted for the production of oligosaccharides, the cell being transformed to comprise at least one nucleic acid sequence coding for an enzyme involved in oligosaccharide synthesis. In addition the cell is transformed to comprise at least one nucleic acid sequence coding for a protein of the sugar efflux transporter family, a functional homolog or derivative thereof. Further, the invention concerns a method for the production of oligosaccharides involving above cell.

10 Claims, 2 Drawing Sheets

(56) References Cited

OTHER PUBLICATIONS

Kretzchmar, G., et al., (2000) Large scale synthesis of linker-modified sailyl-Lewis(X), Lewis(X) and N-acetyllactosamine. Tetrahedron 54: 6341-6358.

Kunz, C., (2000) Oligosaccharides in human milk: structural, functional, and metabolic aspects. Annu Rev Nutr 20: 699-722.

Kunz, C., et al (2006) Health promoting aspects of milk oligosaccharides. Int Dairy J 16: 1341-1346.

Liu Jia Yeu, et al., "Functional and Biochemical Characterization of *Escherichia coli* Sugar Efflux Transporters," The Journal of Biological Chemistry, vol. 274, No. 33, Aug. 13, 1999, pp. 22977-22984.

Liu Jia Yeu, et al., "The Identification of a new family of sugar efflux pumps in *Escherichia coli*," Molecular Microbiology (1999) 31(6), pp. 1845-1851.

Newburg, D. S., (2001) Bioactive components of human milk: evolution, efficiency, and protection. Adv Exp Med Biol 501: 3-10.

Newburg, D. S., et al., (1995) Carbohydrates in milk. In: Handbook of Milk Composition. R. G. Jensen (ed). San Diego, CA: Academic Press, pp. 273-349.

Paulsen, Ian T., et al., "Microbial Genome Analyses: Comparative Trans;prot Capabilities in Eighteen Prokaryotes," J. Mol. Biol. (2000) 301, pp. 75-100.

Ruiz-Palacios, G. M., et al., (2003) *Campylobacter jejuni* binds intestinal H(O) antigen (Fuc alpha 1, 2 Gal beta 1, 4 ClcNAc), and fucosyloligosaccharides of human milk inhibit its binding and infection. J Biol Chem 278: 14112-14120.

Samain, E., (1999) Production of O-acetylated and sulfacted chitooligosaccharides by recombinant *Escherichia coli* strains harboring different combinations of nod genes. J Biotechnol 72: 33-47.

Sambrook, J., et al., (2001) Molecular cloning: a laboratory manual. Cold Spring Harbor Laboratory Press. Cold Spring Harbor, NY.

Vachon, Vincent, et al., "Transmembrane Permeability Channels across the Outer Membrane of *Haemophilus influenza* Type b," Journal of Bacteriology, Jun. 1985, pp. 918-924.

\* cited by examiner

METHOD FOR THE PRODUCTION OF FUCOSYLLACTOSE IN BACTERIAL CELLS

The present invention relates to a cell to be stably cultured in a medium, which cell is adjusted for the production of oligosaccharides, the cell being transformed to comprise at least one nucleic acid sequence coding for an enzyme involved in oligosaccharide synthesis.

Such cells are known for example from Dumon et al., 2001.

It has been long known that human mother's milk, besides lactose, comprises a complex mixture of oligosaccharides called Human Milk Oligosaccharides (HMO). This oligosaccharide fraction of human mother's milk is unique with respect to composition and quantity. In contrast to other mammals, human mother's milk comprises an oligosaccharide concentration ranging from 7 to 12 g/L, which is by a factor of 10 to 100 higher than in most other mammals (Boehm & Stahl, 2007, Kunz et al., 2000, Newburg & Neubauer, 1995).

Today, more than 80 compounds, belonging to HMOs, have been structurally characterized. Generally, HMOs are characterized, unlike other oligosaccharides found in the human body, by a lactose moiety at the reducing end, and fucose and/or sialic acid at the non-reducing end.

Two basic types are distinguished: Oligosaccharides of type I structure have fucose α1,4-linked to GlcNAc, whereas those of type II structure show α1,3-fucosylation of GlcNAc or glucose; either type may contain α1,2-linked fucose to galactose. The most prominent oligosaccharides are 2'-fucosyllactose and 3-fucosyllactose.

These structures are closely related to epitopes of epithelial cell surface glycoconjugates, the Lewis histo-blood group antigens such as Lewis x (Le$^x$) (Gal(β1-4)[Fuc-(α1-3)] GlcNAc(β1)) (Newburg, 2001). The structural homology of HMO to epithelial epitopes accounts for protective properties against bacterial pathogens.

For example, the virulence of pathogenic *Escherichia coli* (Cravioto et al., 1991), *Vibrio cholerae* (Copps et al., 2006), *Streptococcus pneumoniae* (Andersson et al., 1986) or *Campylobacter jejuni* (Ruiz-Palacios et al., 2003) can be drastically reduced by the binding of pathogens to HMO instead of to human mucosal surface glycans, and also the binding to toxins like the heat-stable enterotoxin of *E. coli* (Crane et al., 1994).

Besides the mentioned local effects in the intestinal tract, HMOs are also capable of eliciting systemic effects in infants by entering the systemic circulation (Gnoth et al., 2001). The impact of HMOs on protein-carbohydrate interactions, e.g., selectin-leukocyte binding, can modulate immune responses and reduce inflammatory responses (Bode, 2006, Kunz & Rudloff, 2006).

In order to reduce the frequency of infections acquired by neonates and, therefore, as well infant mortality, it is of course highly desirable to generally provide infants with nutrition including HMOs. This may be easily achieved in societies, where breast-feeding is commonly and widely practiced. This, however, is not generally the case.

There exist a number of medical reasons, like the possible transmission of infectious diseases from mother to child, which under certain circumstances argue against breast feeding. In many African countries, for example, breast feeding may be a major reason for HIV-infections during infancy.

Also cultural circumstances may lead to refusal of breast feeding, as is the case in major industrial countries like, for example, the US.

Due to the fact that HMOs can be found in natural sources, such as the milk of other mammals, only in low concentrations, the extraction of oligosaccharides from natural sources is not suited for satisfying the demand for HMOs.

The chemical synthesis of oligosaccharides is laborious and requires multiple protection and deprotection steps (Kretzschmar & Stahl, 1998), therefore generally being relatively expensive and bearing low recovery-rates.

Therefore, fermentative production of oligosaccharides utilizing biotechnically engineered organisms is a promising alternative solution for large-scale HMO synthesis.

During the past decade, several successful attempts of HMO synthesis using either fermentation with recombinant *E. coli* or in vitro enzymatic conversion, have been published. These attempts have mainly concentrated on synthesizing fucosylated compounds belonging to or closely resembling HMOs.

For example, several publications describe the synthesis of Lewis structures lacto-N-neofucopentaose, lacto-N-neodifucohexaose and lacto-N-neodifucooctaose, as well as 2'- and 3-fucosyllactose (Albermann et al., 2001, Dumon et al., 2006, Dumon et al., 2001, Dumon et al., 2004, Koizumi et al., 2000). In these cases, enzymatic fucosylation of educts like, for example, lactose, is carried out by fucosyltransferases (FucTs).

Most publications reporting production of fucosylated compounds in this connection describe the use of FucTs originating from *Helicobacter pylori*. Generally, human FucTs can as well be utilized for this purpose. However, when overexpressed in bacterial cells, FucTs from bacterial sources are generally less prone for problems such as misfolding and insolubility.

Further, most published systems for the synthesis of fucosylated compounds rely on the endogenous GDP-fucose pool of *E. coli*, which is normally used for the synthesis of the fucose-containing exopolysaccharide colonic acid (Grant et al., 1970). In these cases, the availability of GDP-fucose is of course a bottleneck, restricting synthesis efficiency.

Recently, the inventors of the present invention have described a novel whole-cell production process utilizing the enzyme Fkp (Parkot et al., 2008), the entire contents of this patent application being incorporated herein by reference.

Fkp (Coyne et al., 2005), which originates from *Bacteroides fragilis*, is a bifunctional enzyme, which possesses both fucokinase and L-fucose-1-P-guanylyltransferase activity. Hence, exogenously supplied fucose is first phosphorylated and then nucleotide-activated to form the important precursor molecule GDP-fucose. The Fkp-based L-fucose salvage pathway has been successfully used to synthesize fucosylated oligosaccharides (Parkot et al., 2008).

Even though, on the level of biochemical synthesis as such, important strategies have been developed, the known methods for in vivo oligosaccharide synthesis all bear certain disadvantages, inhibiting, at most, the mass production of oligosaccharides.

The true difficulty in producing, in cells, oligosaccharides at high rates is on one hand the massive intracellular enrichment of the produced oligosaccharides and nucleotide byproducts, and on the other hand the extraction of the produced oligosaccharides.

Due to intracellular enrichment, the products of the synthesis reaction may gradually develop a product-inhibitory effect on the synthetic enzymes. At a certain point, the synthesis thus becomes inefficiently slow. Further, the products may reach cytotoxic concentrations driving the cells into lysis or at least metabolic arrest. In any case, no continuous intracellular production of oligosaccharides is possible.

Further, it can be expected that the accumulation of excessive amounts of oligosaccharides will eventually lead to cell lysis and cell death. This cell lysis or the later performed cell lysis used for the extraction of the synthesized oligosaccharides from the cell will lead to a complex mixture of target oligosaccharides and cell components (metabolites, debris). The purification of the target oligosaccharide from this complex mixture is costly and thus for most oligosaccharides not economical.

Under these circumstances, biotechnical oligosaccharide production is very inefficient and hard to control, especially since known biotechnical oligosaccharide production is performed using batch culturing, such batch culturing being, from the economical point of view, highly unsatisfactory.

In view of the above, it is an object of the invention to improve the methods of biotechnical production of oligosaccharides in such a way that the production is facilitated and made more controllable, and in that generally the output of oligosaccharides is enhanced.

According to the invention, this and other objects are achieved by providing a cell of the kind mentioned at the outset, the cell in addition being transformed to comprise at least one nucleic acid sequence coding for a protein of the sugar efflux transporter family, a functional homolog or derivative thereof.

The object of the invention is thus achieved completely.

According to the invention, oligosaccharides are understood to be short polymers of monosaccharides, comprising at least 2 sugar-subunits. The oligosaccharides may either be branched or form a linear chain of subunits. Moreover, the sugar subunits of oligosaccharides may feature a number of chemical modifications. Accordingly, the oligosaccharides according to the present invention may comprise one or more non-sugar moieties.

Nucleic acid sequence, according to the invention, describes a genetic code, represented by a nucleic acid polymer, like e.g. a desoxyribonucleic acid polymer or a ribonucleic acid polymer. The genetic code may thereby include coding sequences, including information for forming a protein, or non-coding regions comprising for example promoter regions, regions for the attachment of regulatory or auxiliary compounds, spacers and structural sequences influencing the secondary or tertiary structure of the nucleic acid polymer itself and/or participating in its processing.

"Transformed to comprise", according to the present invention, relates to any method of inserting at least one additional nucleic acid sequence into cells, the nucleic acid sequence thereafter being present inside the cell either as a plasmid or being integrated into the cells chromosome/chromosomes. Known transformation methods comprise for example chemical transformation or electroporation. Stable trangenesis, even in the absence of selective agents, can generally be achieved by chromosomal integration of at least one additional nucleic acid sequence. For this purpose, the cell may be infected with a virus or phage. Alternatively, other means of homologous and non-homologous recombination using, for example, virus- or transposon-based systems, may be applied.

For biotechnological applications, the export of larger oligosaccharides from cells is a complex problem. This is primarily the case, because only few cellular mechanisms relating to such transport have been identified. The reason for the infrequent occurrence of oligosaccharide export from cells is that oligosaccharide synthesis is consuming a large amount of cellular resources. The loss of these compounds is therefore generally unfavorable for the cell.

Moreover, the majority of known mechanisms for oligosaccharide export involve the chemical modification of the oligosaccharides, for example by linking them to lipid-moieties (Alaimo et al. 2006). Consequently, the oligosaccharides are not only membrane-borne, inhibiting their release into the medium, but as well chemically linked to lipid-moieties, reducing their solubility in aqueous media. Accordingly, such mechanisms are hardly suited for being employed in large scale production of oligosaccharides.

The Sugar Efflux Transporter (SET) family, first described by Liu and co-workers (Liu et al, 1999a) for *E. coli*, comprises proteins SetA, SetB and SetC. Homologues (amino acid identities >50%) of the transporter proteins are found primarily in Enterobacteriaceae (Liu et al. 1999a).

Besides glucose and lactose, the SET exporter proteins display substrate specificity for certain mono- and di-saccharides as well as, for example, the inducer molecule isopropyl-β-D-thiogalactoside (IPTG) and toxic sugar analogue o-nitrophenyl-β-D-thiogalactoside (ONPG) (Liu et al., 1999b). Biochemical studies showed, however, that, for example, SetA exhibits a very low to zero transport activity for larger or bulkier molecules such as heptoses or trisaccharides.

For above reasons, it could not be expected that exporter proteins of the SET family would be suitable at all for the transport of oligosaccharides.

However, the inventors have found that, surprisingly, the overexpression of SET exporter proteins leads to a very efficient export of oligosaccharides.

Moreover, SET proteins have been shown to export lactose, one of the educts of the synthesis reaction. It was therefore to be expected, that the synthesis of oligosaccharides obtained in the modified cells would proceed very inefficiently and slow due to a constant drain of educt from the cells.

By contrast, the inventors have been able to show for the first time that, despite the overexpression of SET exporter proteins, the synthesis of oligosaccharides obtained in the modified cells is highly productive.

Generally, it is preferred if the cell is selected from the group consisting of bacteria, fungi, animal and plant cells. It is thereby in particular preferred if the cell is an *Escherichia coli* cell.

The advantage hereby is that *E. coli* cells offer high metabolic activity and a high reproduction rate. In addition, *E. coli* is one of the best characterized organisms for molecular biological and biotechnical purposes. Many techniques for the transformation and cultivation of bacteria known in the art have been especially adapted to *E. coli*. In addition, *E. coli* strains with a variety of genetic backgrounds are commercially available.

Further, it is preferred, if the enzyme is selected from the group comprising glycosyltransferase, Leloir type glycosyltransferase, non-Leloir glycosyltransferase, sialyltransferase, galactosyltransferase, fucosyltransferase, mannosyltransferase, N-acetylglucosaminyltransferase, N-acetylgalactosaminyltransferase.

According to one embodiment, the enzyme is a fucosyltransferase.

Moreover, it is preferred, if the sugar efflux transporter is SetA or a derivative there-of.

The advantage in this case is that SetA, amongst the biochemically characterized members of the SET family of exporter proteins, features the widest substrate specificity. Hence, the widest variety of oligosaccharides can, at least potentially be exported and thus produced, using SetA.

It is also preferred, if the cell is further transformed to comprise at least one nucleic acid sequence coding for a protein facilitating or promoting the import of educts required for oligosaccharide synthesis.

Hereby, it is advantageous, that the educt concentration inside the cell is increased. Under normal circumstances, the import of educts such as fucose or lactose is limited by the availability of corresponding importer proteins. In case of a cell adjusted for the large scale synthesis of oligosaccharides, however, the import of educts, relying on endogenous levels of importer proteins, may be insufficient for constantly supplying the synthesis reaction with educts. This problem can be met by overexpressing the respective importer proteins.

Importer proteins with relevance in the present case are primarily importers for mono- or disaccharides such as lactose importers, for example E. coli β-galactoside permease (LacY), or fucose importers, for example E. coli fucose permease (FucP), but as well may comprise importers for nucleotides and other educts.

It is especially preferred, if the cell is transformed to comprise at least one nucleic acid sequence coding for a protein selected from the group consisting of lactose transporter, fucose transporter, sialic acid transporter, galactose transporter, mannose transporter, N-acetylglucosamine transporter, N-acetylgalactosamine transporter, ABC-transporter, transporter for a nucleotide-activated sugar and transporter for a Nucleobase, Nucleoside or Nucleotide.

In this connection, a nucleotide-activated sugar may be, but is not limited to, GDP-fucose, CMP-sialic acid, UDP-galactose, UDP-glucose, GDP-mannose, UDP-glucosamine or UDP-galactosamine.

Further, the term nucleobase stands for Guanin, Cytosin, Adenin, Thymin and Uracil. Nucleoside stands for Guanosin, Cytidin, Adenosin, Thymidin and Uridin whereas a nucleotide may be a mono-, di- or triphosphate of Guanosin, Cytidin, Adenosin, Thymidin or Uridin.

In addition, it is preferred, if the cell is further transformed to comprise at least one nucleic acid sequence coding for a protein selected from the group consisting of nucleotidyltransferase, guanylyltransferase, uridylyltransferase, Fkp, L-fucose kinase, fucose-1-phosphate guanylyltransferase, CMP-sialic acid synthetase, galactose kinase, galactose-1-phosphate uridylyltransferase, glucose kinase, glucose-1-phosphate uridylyltransferase, mannose kinase, mannose-1-phosphate guanylyltransferase, GDP-4-keto-6-deoxy-D-mannose reductase, glucosamine kinase, glucosamine-phosphate acetyltransferase, N-acetyl-glucosamine-phosphate uridylyltransferase, UDP-N-acetylglucosamine 4-epimerase, UDP-N-acetylglucosamine 2-epimerase.

In this connection, the term nucleotidyl transferase generaly relates to enzymes that can transfer nucleotides onto phosphosugars, be it naturally occurring sugars or non-natural sugars.

The advantage hereby is that, as described as well in Parkot et al. 2008, included herein by reference, the intracellular pools of nucleotide-activated sugars like GDP-fucose can be supplemented. Hence, oligosaccharide synthesis is made more efficient.

Moreover, it is generally preferred, if the cell's catabolic pathway for selected mono-, di- or oligosaccharides involved in and/or required for the synthesis of oligosaccharides is at least partially inactivated.

Here, the advantage lies in the fact that the overall synthesis efficiency can be increased. This is the case because less educts destined for oligosaccharide synthesis are consumed by the endogenous metabolism of the cell.

In the embodiment described below, for example, cells are employed, which are deficient in lactose degradation. This can be accomplished by inactivating the enzyme β-galactosidase, which is encoded by the gene lacZ. This genetic modification prevents the intracellular cleavage of lactose into quickly metabolizable monosaccharides glucose and galactose. Thus, lactose is present in higher concentration as acceptor molecule for subsequent glycosylation/fucosylation reactions.

In an alternative embodiment, the cells used for oligosaccharide synthesis are, alone or in addition to the lacZ-deficiency described above, deficient for L-fucose degradation. This can be achieved by inactivating the gene fucA coding for the key catabolic enzyme fuculose-1-phosphate aldolase (FucA) of the fucose degradation pathway.

Of course, there are also other techniques available, ranging from enzymatic inhibitors to stably transfected RNAi constructs, which may be employed in order to at least partially inactivate catabolic pathways.

Within the scope of the present invention, it is generally preferred if the oligosaccharides comprise at least three sub-units and/or feature a molecular weight of at least about 480 g/mol.

All HMOs of major importance have a molecular weight above this threshold.

The present invention further concerns a method for the production of oligosaccharides, comprising the steps of:
a) providing a cell according to the invention,
b) culturing the cell in a medium under conditions permissive for the production of said oligosaccharides,
c) extracting said oligosaccharides from the culture medium.

In the scope of the present invention, permissive conditions are understood to be conditions relating to physical or chemical parameters including but not limited to temperature, pH, pressure, osmotic pressure and product/educt concentration.

In a particular embodiment, the permissive conditions may include a temperature-range of 30+/−20° C., a pH-range of 7+/−3.

The method described above affords the advantage, that oligosaccharides can be extracted directly from the culture medium, whereas the known methods require the lysis of the cells and subsequent extraction of oligosaccharides from the resulting lysate.

In this connection, it is preferred if step b) is performed using a continuous flow bioreactor.

The advantage is that, using a continuous flow bioreactor, the amount of oligosaccharides produced can be easily increased. This is the case, because the synthesis occurs continuously at a relatively high level.

It is also preferred, if the medium in step b) comprises one or more substances selected from the group consisting of basic supplements for supporting cellular growth and propagation, selective agents, effectors of gene activity and educts required for the synthesis of oligosaccharides.

Typical supplements for supporting cellular growth and propagation are extensively known from the prior art and are described for example in Sambrook and Russel, 2001. Such basic supplements account for the general nutritional demand of cultured cells, containing for example proteins, carbohydrates, lipids and minerals.

Also selective agents like antibiotics are extensively known from the prior art, for example Sambrook and Russel, 2001. Such agents can be used in order to protect cultures of genetically modified cells form persisting contamination with competing organisms such as fungi or bacteria. Further, for example in bacterial populations, selective agents may be utilized in order to stabilize the genetic information comprised on a plasmid.

Effectors of gene activity may be used to selectively induce or repress the activity of certain genes or sets of genes within a cell. Such effectors range from simple chemical compounds such as isopropyl-1-thio-β-D-galactopyranoside (IPTG) to more complex compounds like hormones. Such effectors of gene activity are extensively known from the prior art, for example from Sambrook and Russel, 2001.

Further, it is preferred if the educts are selected from the group consisting of arabinose, threose, erythrose, ribose, ribulose, xylose, glucose, D-2-deoxy-2-amino-glucose, N-acetylglucosamine, glucosamine, fructose, mannose, galactose, N-acetylgalactosamine, galactosamine, sorbose, fucose, N-acetylneuraminic acid, glycoside, non-natural sugar, nucleobase, nucleoside, nucleotide and any possible di- or polymer thereof.

It is generally preferred, if the oligosaccharides comprise at least three subunits and/or feature a molecular weight of at least about 480 g/mol.

According to an embodiment of the present invention, the oligosaccharide produced by the method described above is fucosyllactose, the advantage in this case being, that fucosyllactose is one of the most prominent compounds being present in HMOs.

Further advantages follow from the description of the embodiments and the attached drawings.

It goes without saying that the abovementioned features and the features which are still to be explained below can be used not only in the respectively specified combinations, but also in other combinations or on their own, without departing from the scope of the present invention.

Several embodiments of the invention are illustrated in the figures and explained in more detail in the following description. In the figures.

EXAMPLE 1

Figure 1:
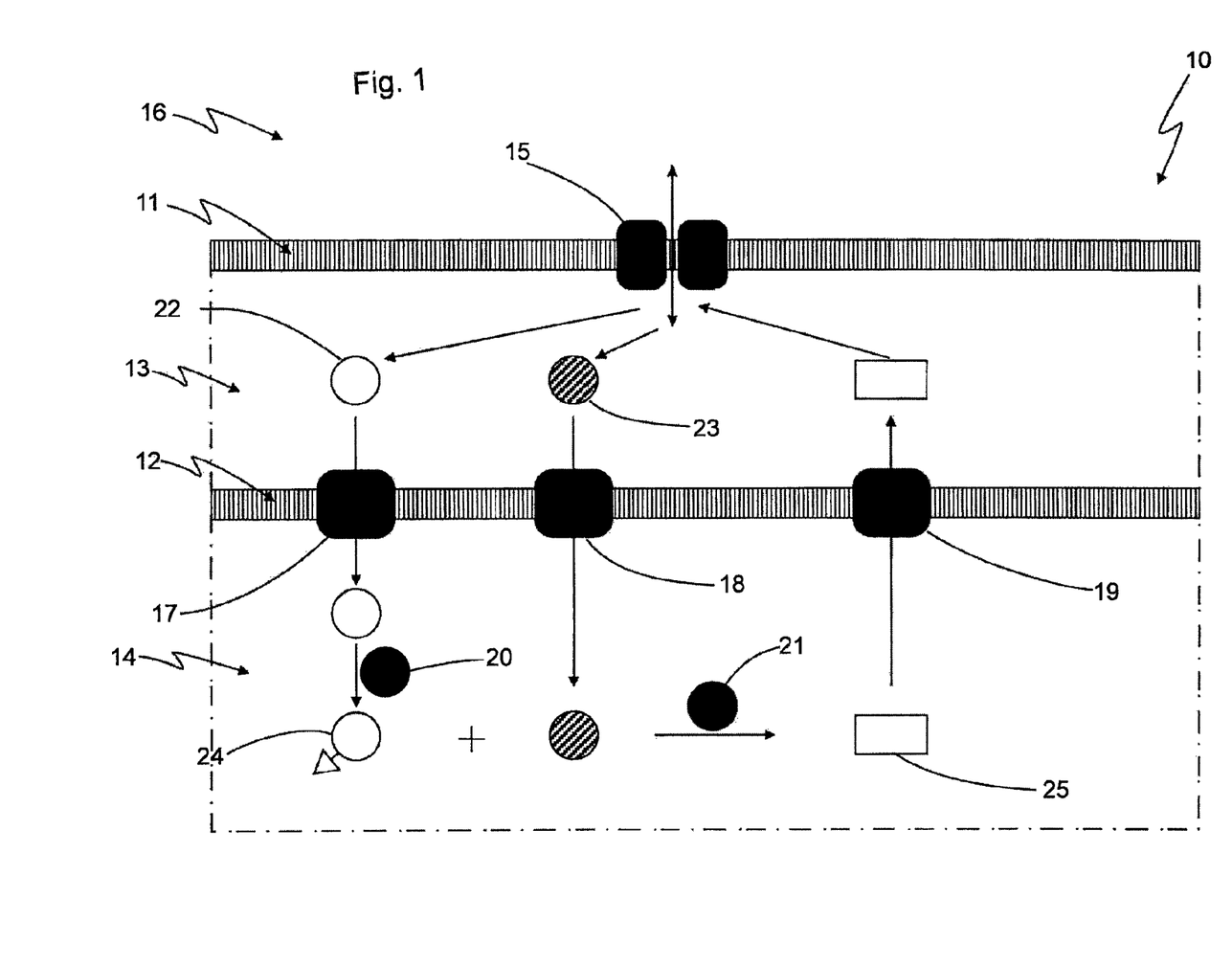
FIG. 1 shows a schematic overview of oligosaccharide synthesis and transport inside a gram negative bacterial cell modified according to the invention.

Oligosaccharide Synthesis and Transport Inside a Gram Negative Bacterial Cell FIG. 1 shows a section of a gram negative bacterial cell 10. A gram negative bacterial cell 10 according to the invention is comprised of an outer membrane 11, a plasma membrane 12, a periplasmic space 13, located in between said outer membrane 11 and said plasma membrane 12, and a cytosol 14, enclosed within said plasma membrane 12. The outer membrane comprises porins through which water-soluble compounds can pass from the medium 16 into the periplasmic space 13 and vice versa.

According to one embodiment of the present invention, the plasma membrane comprises FucP, serving as a first educt-transporter 17, LacY, serving as a second educt transporter 18, and SetA, serving as a product exporter.

Further, Fkp, serving as a nucleotidyltransferase 20, and FutAco, serving as a glycosyltransferase 21, are comprised in the cytosol 14.

When, according to this embodiment, fucose, as a first educt 22, and lactose, as a second educt 23, are supplied to the medium 16, they enter the periplasmic space 13 through the porin 15. Then, the first educt 22 is transported by the first educt transporter 17 into the cytosol 14. In the cytosol, the first educt 22 is modified by the nucleotidyltransferase 20 resulting in a nucleotidylated first educt 24, GDP-fucose.

The second educt 23, is imported into the cytosol 14 by the second educt importer 15.

Then the glycosyltransferase 21 catalyses a reaction between the nucleotidylated first educt, GDP-fucose, and the second educt, lactose, resulting in an oligosaccharide 25, 3-fucosyllactose, and GDP (not shown).

Subsequently, the oligosaccharide 25 is exported from the cytosol 14 by the product exporter 19 (SetA) into the periplasmic space 13 and can leave the periplasmic space 13 via the porins 15, entering the medium 16.

EXAMPLE 2

Material and Methods 2.1 Construction of Expression Plasmids and Development of E. coli Strains E. coli JM109(DE3) (Promega) was used as initial host strain for the development of the E. coli production strain. All oligonucleotide primers used for the cloning procedures are listed in Table 1. Plasmids pACYC-lacY and pACYC-lacY-setA were constructed as follows: The genes lacY (corresponds to GenBank accession no. ACB02461) and setA (corresponds to GenBank accession no. YP_025293) (GenBank) were amplified from genomic DNA of E. coli TOP10(Invitrogen; www.invitrogen.com) using primers lacY NcoI forward/lacY EcoRI reverse and setA NdeI forward/setA XhoI reverse. The PCR products were subjected to restriction digest with the indicated enzymes, and ligated with the correspondingly digested expression vector pACYCDuet-1 (Novagen).

The resulting plasmids were checked by restriction digest, agarose gel electrophoresis as well as sequencing with primers pACYCduetUP1, DuetDOWN-1-Primer, DuetUP2-Primer and T7-Terminator-Primer for the correct insertion of the genes (data not shown). The utilized plasmids pCOLA-fkp-fucP and pET-futAco have previously been constructed (Parkot et al., 2008). To obtain the strains JM00, JM01 and JM02, different combinations of plasmids were introduced into E. coli JM109(DE3) by electroporation (Dower et al., 1988). All plasmids and bacterial strains are listed in Table 2.

2.2 Inactivation of the Fucose-Catabolism in E. coli:

To prevent the degradation of externally supplied fucose, the fucA gene coding for the key catabolic enzyme L-fuculose-1-phosphate aldolase was deleted from the chromosome of E. coli JM109(DE3). All oligonucleotide primers used for the mutagenesis procedures are listed in Table 1. For construction of the fucA deletion mutant, the methodology of Datsenko and Wanner was applied (Datsenko and Wanner, 2000), using the primers fucA-knock-f and fucA-knock-r. The correct deletion of fucA was confirmed by PCR using primers fucA-control-f and fucA-control-r flanking the chromosomal insertion site, and the fucose-negative phenotype was verified by plating the bacteria on M9 minimal agar (Sambrook and Russell, 2001) with supplemented fucose as the sole carbon source (data not shown).

TABLE 1

Primers used in this study.

| Name | Sequence (5'→3')* | Added restriction site |
|---|---|---|
| fucA-knock-f | AATTACTCTTCAATTCGTAACCCATAGGTTTTGAATTTCT CCAGCACTACGGCAATCTCTTCATCGCTCAGCAGTGTA GGCTGGAGCTGCTTCGAAGTTC | |

TABLE 1-continued

Primers used in this study.

| Name | Sequence (5'→3')* | Added restriction site |
|---|---|---|
| fucA-knock-r | GGTGGGTAATTAAACGGCTAATTCAATAGTGTGAAAG GAACAACATTATTGCCCTGTTTTGAATCAGAGAGAGGG CTGACATGGGAATTAGCCATGGTCC | |
| fucA-control-f | CATTCTGTTAGCCATCATCCTTCTCC | |
| fucA-control-r | GAAGAAGATGGTGGGTAATTAAACGGC | |
| setA NdeI forward | AAGGGAAAAA<u>CATATG</u>ATCTGGATAATGAC GATGGCTCGCCGTATGAACGGTG | NdeI |
| setA XhoI reverse | AAGGGAAAAA<u>CTCGAG</u>CCACGTCATCAAACGTCTTTAA CCTTTGCGG | XhoI |
| lacY NcoI forward | AAGGAAATATA<u>CCATGG</u>GCTACTATTTAAAAAACACAA ACTTTTGGATGTTCGG | NcoI |
| lacY EcoRI reverse | AAGGAAAACC<u>GAATTC</u>GATTGCTTAAGCGACTTCATTC ACCTGACGACGCAGCAGGG | EcoRI |
| pACYCduetUP1 | GGATCTCGACGCTCTCCCT | |
| DuetDOWN-1-Primer | GATTATGCGGCCGTGTACAA | |
| DuetUP2-Primer | TTGTACACGGCCGCATAATC | |
| T7-Terminator-Primer | TATGCTAGTTATTGCTCAG | |

*Restriction endonuclease recognition sites are underlined.

TABLE 2

Bacterial strains and plasmids used in this study.

| Name | Relevant characteristic(s)* | References |
|---|---|---|
| *E. coli* strains | | |
| TOP10 | F- mcrA, Δ(mrr-hsdRMS-mcrBC), φ80lacZΔM15, ΔlacX74, recA1, araD139, Δ(araleu) 7697 galU galK rpsL (StrR) endA1 nupG | Invitrogen |
| JM109(DE3) | endA1, recA1, gyrA96, thi, hsdR17 ($r_k^-$, $m_k^+$), relA1, supE44, λ-, Δ(lac-proAB), [F', traD36, proAB, lacI$^q$ZΔM15], IDE3 | Promega |
| JM109(DE3)ΔfucA | JM109(DE3) fucA deletion mutant | This study |
| JM00 | Negative control strain, JM109(DE3) harboring empty vectors pCOLADuet-1, pETDuet-1 and pACYCDuet-1 | This study |
| JM01 | JM109(DE3) harboring pCOLA-fkp-fucP, pET-futAco and pACYC-lacY | This study |
| JM02 | JM109(DE3) harboring pCOLA-fkp-fucP, pET-futAco and pACYC-lacY-setA | This study |
| JM03 | JM109(DE3) harboring pCOLA-fkp-fucP and pACYC-lacY-setA | This study |
| JMΔ00 | Negative control strain, JM109(DE3) ΔfucA harboring empty vectors pCOLADuet-1, pETDuet-1 and pACYCDuet-1 | This study |
| JMΔ01 | JM109(DE3) ΔfucA harboring pCOLA-fkp-fucP, pET-futAco and pACYC-lacY | This study |
| JMΔ02 | JM109(DE3) ΔfucA harboring pCOLA-fkp-fucP, pET-futAco and pACYC-lacY-setA | This study |
| JMΔ03 | JM109(DE3) ΔfucA harboring pCOLA-fkp-fucP and pACYC-lacY-setA | This study |
| Plasmids | | |
| pCOLADuet-1 | expression vector, Km$^R$ | Novagen |
| pETDuet-1 | expression vector, Ap$^R$ | Novagen |
| pACYCDuet-1 | expression vector, Cm$^R$ | Novagen |
| pCOLA-fkp-fucP | harboring genes fkp and fucP, Km$^R$ | Parkot et al., 2008 |
| pET-futAco | harboring codon-optimized fucosyltransferase gene futAco of *H. pylori*, Ap$^R$ | Parkot et al., 2008 |
| pACYC-lacY | harboring gene lacY, Cm$^R$ | This study |
| pkCYC-lacY-setA | harboring genes lacY and setA, Cm$^R$ | This study |

Ap$^R$, ampicillin resistant; Km$^R$, kanamycin resistant; Cm$^R$, chloramphenicol resistant.

2.3 Culture Conditions and Preparation of Cell Extracts

E. coli strains were inoculated 1:100 from overnight cultures in 100 mL of mineral medium (Samain et al., 1999), containing 7.0 g L$^{-1}$ NH$_4$H$_2$PO$_4$, 7.0 g L$^{-1}$ K$_2$HPO$_4$, 1.0 g L$^{-1}$ MgSO$_4 \times$7H$_2$O, 0.5 g L$^{-1}$ citric acid, 2.0 g L$^{-1}$ KOH, 0.0045 g L$^{-1}$ thiamine.HCl and 7.5 mL L$^{-1}$ trace mineral solution. The trace mineral stock solution contained 70 mM nitrilotriacetate (pH 6.5), 7.5 g L$^{-1}$ ferric citrate, 1.3 g L$^{-1}$ MnCl$_2 \times$4H$_2$O, 0.21 g L$^{-1}$ CoCl$_2 \times$6H$_2$O, 0.13 g L$^{-1}$ CuCl$_2 \times$2H$_2$O, 0.25 g L$^{-1}$ H$_3$BO$_3$, 1.2 g L$^{-1}$ ZnSO$_4 \times$7H$_2$O and 0.15 g L$^{-1}$ Na$_2$MoO$_4 \times$2H$_2$O. The medium was supplemented with 0.1% glucose and 1% glycerol as carbon source, and with 100 µg mL$^{-1}$ ampicillin, 50 µg mL$^{-1}$ kanamycin and/or 20 µg mL$^{-1}$ chloramphenicol before incubation in a rotary shaker at 37° C. providing good aeration.

When the cultures reached an optical density (OD$_{600\ nm}$) of approximately 1.0, the inducer isopropyl-1-thio-β-D-galactopyranoside (IPTG) was added in a concentration of 0.5 mM, and the cultures were incubated overnight at 28° C. under constant shaking. After approximately 16 hours, 40 mM L-fucose and 20 mM lactose were added. The cultures were then continuously incubated at 28° C. under constant shaking.

At several time points, 20 mL samples of the cultures were collected, and cells were harvested by centrifugation. The culture supernatants were separated and immediately analyzed by high performance anion exchange chromatography (HPAEC) or stored at −20° C. The cell pellets were washed with PBS (Sambrook and Russell, 2001), resuspended in 5 times the pellet weight of distilled water, and lyzed by boiling for 10 min. To obtain intracellular fractions, the cell debris was separated by centrifugation and the clear cell lysate was stored at −20° C. or immediately analyzed by HPAEC.

2.4 SDS-PAGE

The expression of heterologous proteins was checked by SDS-PAGE (Sambrook and Russell, 2001) (data not shown). Protein extracts were prepared in 1× SDS gel-loading buffer, and polyacrylamide gels were stained with Coomassie Brilliant Blue.

2.5 Detection of Oligosaccharides by High Performance Anion Exchange Chromatography with Pulsed Amperometric Detection (HPAEC-PAD)

Samples were analyzed by high performance anion exchange chromatography (HPAEC) using a Decade II pulsed amperometric detector (PAD) (Antec Leyden) and a CarboPac PA20 column (Dionex) connected to a HPLC system (Shimadzu; www.shimadzu.eu). The detector sensitivity was set at 50 µA with a 0.05-V applied pulse potential.

Mono-, di-, and oligosaccharides eluted with 10 mM sodium hydroxide at a flow rate of 0.4 mL min$^{-1}$. After 30 min isocratic elution with 10 mM NaOH the column was washed for 20 min with 200 mM NaOH to obtain constant retention times and thereafter regenerated with 10 mM NaOH for 20 min. For all analyzed samples, 20 µL of 1:2 dH$_2$O-diluted solutions were used for HPAEC analysis. Analysis via HPAEC-PAD showed retention times on the used HPLC column of approximately 3.5 min for the L-fucose standard, approx. 15 min for the lactose standard, and approx. 11-12 min for the 3-fucosyllactose standard (data not shown). Standards of the substances glycerol and glucose, which are added to the culture medium as carbon source, were recorded with a retention time of approx. 1.5 min and 7-8 min, respectively.

EXAMPLE 3

Production of 3-Fucosyllactose and Seta-Dependent Secretion into the Culture Medium by Recombinant E. coli The aim of this experiment was the investigation of SetA-mediated export of intracellular 3-fucosyllactose. E. coli strains JM01 and JM02 (see Table 2) were used for fermentation experiments. The strains JM01 and JM02, which both express the enzymes Fkp and FutAco (α1,3-fucosyltransferase) as well as the transporter proteins FucP and LacY, only differ in expression of the SetA transporter. JM01 is not over-producing SetA, and JM02 is overproducing SetA.

Figure 2:
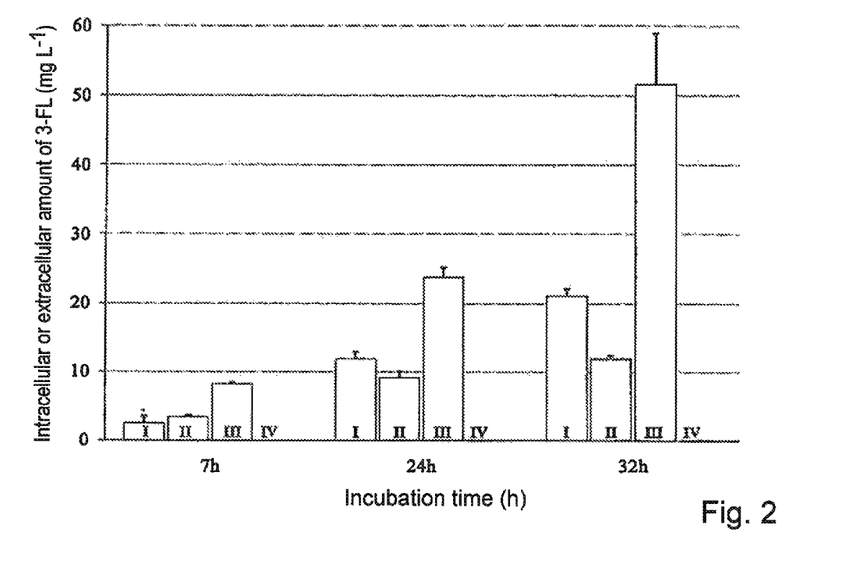
FIG. 2 shows the results of 3-fucosyllactose-measurements in the cellular moist mass and supernatants of bacterial cultures, comparing different genotypes.

FIG. 2 shows the amounts of 3-fucosyllactose in the moist cell mass and supernatant of E. coli cultures JM01 and JM02 determined by HPAEC-PAD analysis.

For determining the effect of SetA overexpression, measurements were performed 7, 24 and 32 hours post induction of fkp, fucP, lacY, futAco and setA expression.

In the figure, extracellular fractions of 3-fucosyllactose measured in E. coli JM01 (SetA not overexpressed) are represented by columns I, the intracellular fractions being represented by columns II. In case of E. coli JM02 (SetA-overexpressed), the extracellular fractions of 3-fucosyllactose are represented by columns III and intracellular fractions are represented by columns IV. All values represent the mean values from duplicate experiments, the error bars indicating the respective standard deviations.

These measurements show, that strain JM01, which does not overexpress SetA, accumulates 3-fucosyllactose in the cytosolic fraction.

By contrast, the intracellular concentration of 3-fucosyllactose in the case of strain JM002, overexpressing setA, is below detection level.

Further, the supernatants from JM01- and JM02-culures exhibit a certain content of 3-fucosyllactose. Thereby, however, the content of 3-fucosyllactose found in the supernatant of the JM02 culture is greatly increased over the content of 3-fucosyllactose found in the supernatant of the JM01 culture. While after 32h, the concentration of 3-fucosyllactose in the supernatant of JM01 is approximately 21 mg L$^{-1}$, the 3-fucosyllactose concentration in the case of JM02 is above 51 mg L$^{-1}$.

Figure 3:
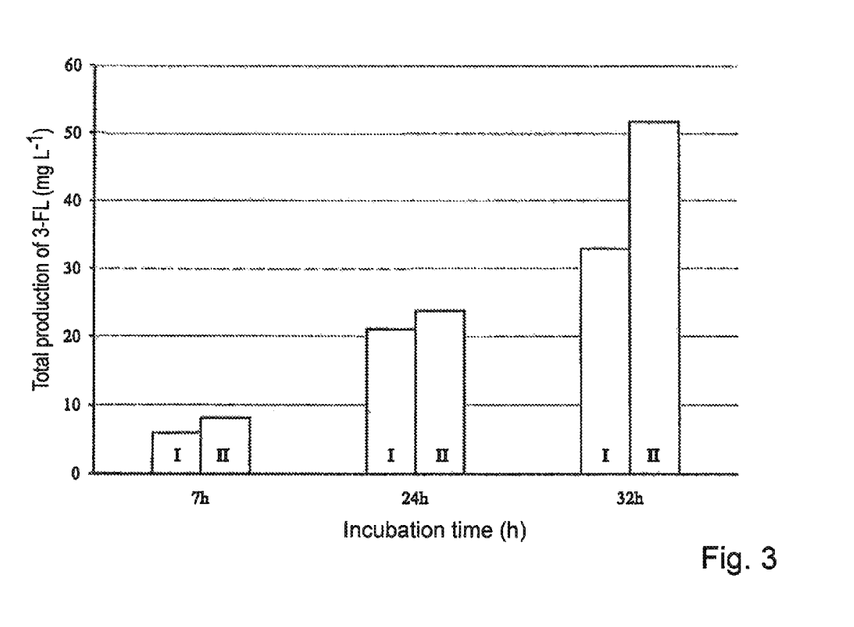
FIG. 3 shows a comparison between the amounts of 3-fucosyllactose synthesized in bacterial cultures with different genotypes.

The comparison of the total amounts of 3-fucosyllactose in cultures of E. coli JM01 and JM02 is depicted in FIG. 3.

Here the total amount of 3-fucosyllactose in E. coli JM01 cultures is represented by columns I and the total amount of 3-fucosyllactose in E. coli JM02 cultures is represented by columns II. Again, mean values from duplicate experiments are displayed.

After 32 h of incubation, the strain JM02 produces with 51.68 mg L$^{-1}$ approximately 57% more 3-fucosyllactose in total than strain JM01 (32.99 mg L$^{-1}$).

EXAMPLE 4

Discussion

The experimental results of the HPAEC-PAD analysis show, that strong differences in synthesis and transport of 3-fucosyllactose exist in between the strains JM01, without SetA overexpression, and JM02, overexpressing SetA.

To start with, 3-fucosyllactose is not detectable in the cellular moist mass of the JM02 culture, whereas a high concentration of 3-fucosyllactose can be measured in the supernatant.

This clearly indicates that the overexpression of SetA in E. coli leads to an extremely efficient export of 3-fucosyllactose from the cell.

Hence, the inventors have shown, that SetA, contrary to what was to be expected from the prior art, can efficiently export larger oligosaccharides featuring, in the present case, three subunits and a molecular mass of 488 g/mol.

By contrast, in the moist cell mass of the JM01, a considerable amount of 3-fucosyllactose is detected, whereas only comparably little 3-fucosyllactose is present in the supernatant.

This result shows that, in absence of overexpressed SetA, 3-fucosyllactose strongly accumulates in the cytosol of the bacterial cells. The fact that also under these circumstances 3-fucosyllactose is detected in the supernatant can, according to the current state of knowledge, be attributed to increased lysis of bacterial cells resulting from high intracellular 3-fucosyllactose concentrations.

When comparing the overall amounts of 3-fucosyllactose in the JM01- and JM02-cultures, it becomes evident that the overexpression of SetA not only leads to increased concentration of 3-fucosyllactose in the supernatant, but also heightens the total amount of synthesized 3-fucosyllactose (see FIG. 3).

This increase in overall synthesis efficiency can be attributed to a higher cell viability of the cells overexpressing SetA, which viability would be due to the avoidance of product-cytotoxicity. Alternatively or in addition, the increase in overall synthesis efficiency can also be attributed to the avoidance of product-inhibitory effects on the synthetic enzymes due to product-export mediated by overexpressed SetA.

Hence, the inventors have shown that overexpression of the SetA transporter is an efficient way to enhance the output of oligosaccharide synthesis, accomplished by biotechnical methods employing culturable cells. Further, as product-inhibition of the relevant synthetic enzymes and cytotoxicity of the synthesis product can be mostly avoided, the production is facilitated and made more controllable.

LIST OF REFERENCES

Alaimo, C., Catrein, I., Morf, L., Marolda, C. L., Callewaert, N., Valvano, M. A., Feldman, M. F. & M. Aebi, (2006) Two distinct but interchangeable mechanisms for flipping of lipid-linked oligosaccharides. EMBO J. 25(5): 967-976.

Albermann, C., W. Piepersberg & U. F. Wehmeier, (2001) Synthesis of the milk oligosaccharide 2'-fucosyllactose using recombinant bacterial enzymes. Carbohydr Res 334: 97-103.

Andersson, B., O. Porras, L. A. Hanson, T. Lagergard & C. Svanborg-Eden, (1986) Inhibition of attachment of Streptococcus pneumoniae and Haemophilus influenzae by human milk and receptor oligosaccharides. J Infect Dis 153: 232-237.

Bode, L., (2006) Recent advances on structure, metabolism, and function of human milk oligosaccharides. J Nutr 136: 2127-2130.

Boehm, G. & B. Stahl, (2007) Oligosaccharides from milk. J Nutr 137: 847S-849S.

Coppa, G. V., L. Zampini, T. Galeazzi, B. Facinelli, L. Ferrante, R. Capretti & G. Orazio, (2006) Human milk oligosaccharides inhibit the adhesion to Caco-2 cells of diarrea pathogens: Escherichia colt Vibrio cholerae, and Salmonella fyris. Pediatr Res 59: 377-382.

Coyne, M. J., B. Reinap, M. M. Lee & L. E. Comstock, (2005) Human symbionts use a host-like pathway for surface fucosylation. Science 307: 1778-1781.

Crane, J. K., S. S. Azar, A. Stam & D. S, Newburg, (1994) Oligosaccharides from human milk block binding and activity of the Escherichia coli heat-stable enterotoxin (STa) in T84 intestinal cells. J Nutr 124: 2358-2364.

Cravioto, A., A. Tello, H. Villafan, J. Ruiz, S. del Vedovo &J. R. Neeser, (1991) Inhibition of localized adhesion of enteropathogenic Escherichia coli to HEp-2 cells by immunoglobulin and oligosaccharide fractions of human colostrum and breast milk. J Infect Dis 163: 1247-1255.

Datsenko, K. A., and B. L. Wanner. 2000. One-step inactivation of chromosomal genes in Escherichia coli K-12 using PCR products. Proc Natl Acad Sci USA 97:6640-5.

Dower, W. J., J. F. Miller, and C. W. Ragsdale. 1988. High efficiency transformation of E. coli by high voltage electroporation. Nucleic Acids Res 16:6127-45.

Dumon, C, C. Bosso, J. P. Utille, A. Heyraud & E. Samain, (2006) Production of Lewis x tetrasaccharides by metabolically engineered Escherichia coli. Chembiochem 7: 359-365.

Dumon, C, B. Priem, S. L. Martin, A. Heyraud, C. Bosso & E. Samain, (2001) In vivo fucosylation of lacto-N-neotetraose and lacto-N-neohexaose by heterologous expression of Helicobacter pylori alpha-1,3 fucosyltransferase in engineered Escherichia coli. Glycoconj J 18: 465-474.

Dumon, C, E. Samain & B. Priem, (2004) Assessment of the two Helicobacter pylori alpha-1,3-fucosyltransferase ortholog genes for the large-scale synthesis of LewisX human milk oligosaccharides by metabolically engineered Escherichia coli. Biotechnol Prog 20:412-419.

Gnoth, M. J., S. Rudloff, C. Kunz & R. K. Kinne, (2001) Investigations of the in vitro transport of human milk oligosaccharides by a Caco-2 monolayer using a novel high performance liquid chromatography-mass spectrometry technique. J Biol Chem 276: 34363-34370.

Grant, W. D., I. W. Sutherland & J. F. Wilkinson, (1970) Control of colanic acid synthesis. J Bacteriol 103: 89-96.

Koizumi, S., T. Endo, K. Tabata, H. Nagano, J. Ohnishi & A. Ozaki, (2000) Large-scale production of GDP-fucose and Lewis X by bacterial coupling. J Ind Microbiol Biotechnol 25: 213-217.

Kretzschmar, G. & W. Stahl, (1998) Large scale synthesis of linker-modified sialyl-Lewis(X), Lewis(X) and N-acetyl-lactosamine. Tetrahedron 54: 6341-6358.

Kunz, C. & S. Rudloff, (2006) Health promoting aspects of milk oligosaccharides. Int Dairy J 16: 1341-1346.

Kunz, C., S. Rudloff, W. Baier, N. Klein & S. Strobel, (2000) Oligosaccharides in human milk: structural, functional, and metabolic aspects. Annu Rev Nutr 20: 699-722.

Liu, J. Y., P. F. Miller, M. Gosink & E. R. Olson, (1999a) The identification of a new family of sugar efflux pumps in Escherichia coli. Mol Microbiol 31:1845-1851.

Liu, J. Y., P. F. Miller, J. Willard & E. R. Olson, (1999b) Functional and biochemical characterization of Escherichia coli sugar efflux transporters. Journal of Biological Chemistry 214: 22977-22984.

Newburg, D. S., (2001) Bioactive components of human milk: evolution, efficiency, and protection. Adv Exp Med Biol 501: 3-10.

Newburg, D. S. & S. H. Neubauer, (1995) Carbohydrates in milk. In: Handbook of Milk Composition. R. G. Jensen (ed). San Diego, Calif.: Academic Press, pp. 273-349.

Parkot, J., E. Hüfner & S. Jennewein, (2008) Synthesis of fucosylated compounds. European patent application EP08172267.

Ruiz-Palacios, G. M., L. E. Cervantes, P. Ramos, B. Chavez-Munguia & D. S, Newburg, (2003) Campylobacter jejuni binds intestinal H(O) antigen (Fuc alpha 1, 2 Gal beta 1, 4 GlcNAc), and fucosyloligosaccharides of human milk inhibit its binding and infection. J Biol Chem 278: 14112-14120.

Samain, E., V. Chazalet & R. A. Geremia, (1999) Production of O-acetylated and sulfated chitooligosaccharides by recombinant Escherichia coli strains harboring different combinations of nod genes. J Biotechnol 72: 33-47.

Sambrook, J. & D. W. Russell, (2001) Molecular cloning: a laboratory manual. Cold Spring Harbor Laboratory Press, Cold Spring Harbor, N.Y.

The invention claimed is:

1. Method for the production of fucosyllactose, comprising the steps of:
   a) providing a bacterial cell transformed to comprise at least one nucleic acid sequence coding for fucosyltransferase, and transformed to comprise at least one nucleic acid sequence coding for a protein of the sugar efflux transporter (SET) family, wherein the protein of the SET family is overexpressed in said bacterial cell,
   b) culturing the bacterial cell in a medium under conditions permissive for the production of fucosyllactose, whereby the fucosyllactose is exported into the medium; and
   c) extracting said fucosyllactose from the medium.

2. Method according to claim 1, characterized in that step b) is performed using a continuous flow bioreactor.

3. Method according to claim 1, characterized in that, the medium in step b) comprises educts required for the synthesis of oligosaccharides, wherein the educts are selected from the group consisting of arabinose, threose, erythrose, ribose, ribulose, xylose, glucose, D-2-deoxy-2-amino-glucose, N-acetylglucosamine, glucosamine, fructose, mannose, galactose, N-acetylgalactosamine, galactosamine, sorbose, fucose, lactose, N-acetylneuraminic acid, glycoside, non-natural sugar, nucleobase, nucleoside, nucleotide and any possible di- or polymer thereof.

4. Method according to claim 1, wherein the bacterial cell is an *Escherichia coli* cell.

5. Method according to claim 1, wherein the sugar efflux transporter is SetA or a derivative thereof.

6. Method according to claim 1, wherein the cell is further transformed to comprise at least one nucleic acid sequence coding for a protein facilitating or promoting the import of educts required for oligosaccharide synthesis, wherein the protein is selected from the group consisting of lactose transporter, fucose transporter, sialic acid transporter, galactose transporter, mannose transporter, N-acetylglucosamine transporter, N-acetylgalactosamine transporter, ABC-transporter.

7. Method according to claim 1, wherein the cell is further transformed to comprise at least one nucleic acid sequence coding for a protein selected from the group consisting of nucleotidyltransferase, guanylyltransferase, uridylyltransferase, Fkp, L-fucose kinase, fucose-1-phosphate guanylyltransferase, CMP-sialic acid synthetase, galactose kinase, galactose-1-phosphate uridylyltransferase, glucose kinase, glucose-1-phosphate uridylyltransferase, mannose kinase, mannose-1-phosphate guanylyltransferase, GDP-4-keto-6- deoxy-D-mannose reductase, glucosamine kinase, glucosamine-phosphate acetyltransferase, N-acetyl-glucosamin-phosphate uridylyltransferase, UDP-N-acetylglucosamine 4-epimerase, UDP-N-acetylglucosamine 2-epimerase.

8. Method for the production of fucosyllactose, comprising the steps of:
   a) providing a bacterial cell transformed to comprise at least one nucleic acid sequence coding for a fucosyltransferase, and transformed to comprise at least one nucleic acid sequence coding for a protein of the Sugar Efflux Transporter (SET) family, wherein the nucleic acid sequence coding for the fucosyltransferase and the nucleic acid coding for said protein of the SET family have been exogenously inserted into the bacterial cell; and wherein said protein of the SET family is overexpressed;
   b) culturing the bacterial cell in a medium under conditions permissive for the production of fucosyllactose, whereby the fucosyllactose is exported by the protein of the SET family from the cell into the medium; and
   c) extracting said fucosyllactose from said medium.

9. Method for the production of fucosyllactose, comprising the steps of:
   a) providing *Escherichia coli* cells transformed to comprise at least one nucleic acid sequence coding for a 1,3-fucosyltransferase, and transformed to comprise at least one nucleic acid sequence coding for a protein of the Sugar Efflux Transporter (SET) family, wherein the protein is SetA, wherein the nucleic acid sequence coding for the 1,3 fucosyltransferase and the nucleic acid coding for SetA have been exogenously inserted into the *Escherichia coli* cells, and wherein the protein SetA is overexpressed;
   b) culturing the *Escherichia coli* cells in a medium under conditions permissive for the production of fucosyllactose, whereby the fucosyllactose is exported into the medium; and
   c) extracting fucosyllactose from said medium.

10. Method for the production of fucosyllactose, comprising the steps of:
   a) providing a bacterial cell having a cytosol and transformed to synthesize fucosyllactose and transformed to overexpress an exporter for said fucosyllactose, the exporter being capable of exporting said fucosyllactose from the cytosol of said bacterial cell;
   b) culturing said bacterial cell in a medium under conditions permissive for the production of fucosyllactose, whereby the fucosyllactose is exported into the medium; and
   c) extracting fucosyllactose from said medium.

* * * * *

SEQUENCE LISTING

<160> NUMBER OF SEQ ID NOS: 12

<210> SEQ ID NO 1
<211> LENGTH: 100
<212> TYPE: DNA
<213> ORGANISM: Escherichia coli

<400> SEQUENCE: 1
aattactctt caattcgtaa cccataggtt ttgaatttct ccagcactac ggcaatctct      60
tcatcgctca gcagtgtagg ctggagctgc ttcgaagttc                          100

<210> SEQ ID NO 2
<211> LENGTH: 100
<212> TYPE: DNA
<213> ORGANISM: Escherichia coli

<400> SEQUENCE: 2
ggtgggtaat taaacggcta attcaatagt gtgaaaggaa caacattatt gccctgtttt      60
gaatcagaga gagggctgac atgggaatta gccatggtcc                          100

<210> SEQ ID NO 3
<211> LENGTH: 26
<212> TYPE: DNA
<213> ORGANISM: Escherichia coli

<400> SEQUENCE: 3
cattctgtta gccatcatcc ttctcc                                          26

<210> SEQ ID NO 4
<211> LENGTH: 27
<212> TYPE: DNA
<213> ORGANISM: Escherichia coli

<400> SEQUENCE: 4
gaagaagatg gtgggtaatt aaacggc                                         27

<210> SEQ ID NO 5
<211> LENGTH: 53
<212> TYPE: DNA
<213> ORGANISM: Escherichia coli

<400> SEQUENCE: 5
aagggaaaaa catatgatct ggataatgac gatggctcgc cgtatgaacg gtg            53

<210> SEQ ID NO 6
<211> LENGTH: 47
<212> TYPE: DNA
<213> ORGANISM: Escherichia coli

<400> SEQUENCE: 6
aagggaaaaa ctcgagccac gtcatcaaac gtctttaacc tttgcgg                   47

<210> SEQ ID NO 7
<211> LENGTH: 54
<212> TYPE: DNA
<213> ORGANISM: Escherichia coli

<400> SEQUENCE: 7
aaggaaatat accatgggct actatttaaa aaacacaaac ttttggatgt tcgg           54

```
<210> SEQ ID NO 8
<211> LENGTH: 57
<212> TYPE: DNA
<213> ORGANISM: Escherichia coli

<400> SEQUENCE: 8
aaggaaaacc gaattcgatt gcttaagcga cttcattcac ctgacgacgc agcaggg      57

<210> SEQ ID NO 9
<211> LENGTH: 19
<212> TYPE: DNA
<213> ORGANISM: Escherichia coli

<400> SEQUENCE: 9
ggatctcgac gctctccct                                                19

<210> SEQ ID NO 10
<211> LENGTH: 20
<212> TYPE: DNA
<213> ORGANISM: Escherichia coli

<400> SEQUENCE: 10
gattatgcgg ccgtgtacaa                                               20

<210> SEQ ID NO 11
<211> LENGTH: 20
<212> TYPE: DNA
<213> ORGANISM: Escherichia coli

<400> SEQUENCE: 11
ttgtacacgg ccgcataatc                                               20

<210> SEQ ID NO 12
<211> LENGTH: 19
<212> TYPE: DNA
<213> ORGANISM: Escherichia coli

<400> SEQUENCE: 12
tatgctagtt attgctcag                                                19
```